United States Patent
Dreckmann-Behrendt et al.

[11] Patent Number: 6,166,045
[45] Date of Patent: *Dec. 26, 2000

[54] TORASEMIDE OF MODIFICATION III

[75] Inventors: Bruno Dreckmann-Behrendt, Mannheim, Germany; Artur Burger, Giessenbach; Judith M. Rollinger, Innsbrick, both of Austria

[73] Assignee: Roche Diagnostics GmbH, Mannheim, Germany

[ * ] Notice: This patent is subject to a terminal disclaimer.

[21] Appl. No.: 09/089,066

[22] Filed: Jun. 2, 1998

[51] Int. Cl.[7] .......................... C07D 213/71; A61K 31/44

[52] U.S. Cl. ............................................ 514/347; 546/294

[58] Field of Search ................................ 546/294; 514/347

[56] References Cited

U.S. PATENT DOCUMENTS

| Re. 34,580 | 4/1994 | Topfmeier et al. | 546/291 |
| Re. 34,672 | 7/1994 | Topfmeier et al. | 514/347 |
| 4,018,929 | 4/1977 | Delarge et al. | 514/347 |
| 5,914,336 | 6/1999 | Dreckmann-Behrendt | 514/347 |

*Primary Examiner*—Alan L. Rotman
*Attorney, Agent, or Firm*—Arent Fox Kniter Plotkin & Kahn PLLC

[57] ABSTRACT

A new modification of torasemide, named modification III, has been discovered. Modification III is storage stable and achieves high levels in serum shortly after oral administration. Torasemide of modification III can be used to produce a diuretic effect. A method of making torasemide of modification III is disclosed.

19 Claims, 2 Drawing Sheets

TORASEMIDE/RAT, FEMALE/3 mg/kg p.o.

TORASEMIDE OF MODIFICATION III

BACKGROUND OF THE INVENTION

Torasemide is a known compound which has been approved by the U.S. Food and Drug Administration for use as a diuretic.

Torasemide (1-isopropyl-3-[(4-m-toluidino-3pyridyl) sulphonyl)urea) is a compound with interesting pharmacological properties which is described in Example 71 of U.S. Pat. No. Re 30,633 as 3-isopropylcarbarmylsulfonamido-4-(3'-methyl)-phenylaminopyridine. In particular, this compound belongs to the class of loop diuretics as it blocks the sodium-potassium-2 chloride transport mechanism in the ascending limb of the loop of Henle. in contrast to other standard loop diuretics, however, it shows a less intense initial diuresis and a sustained duration of action.

In the preparation of torasemide, a purification is normally included in which the compound in question is dissolved in an aqueous or aqueous alcoholic solution of sodium hydrogen carbonate and, after filtering off from impurities, the torasemide is again precipitated out with an inorganic acid. In the case of this process, the product is obtained in the form of white crystals with a melting point of 163°–164° C. U.S. Pat. No. Re 30,633 does not mention any particular crystalline form of torasemide.

From Acta Cryst. 1978, pp. 2659–2662 and Acta Cryst., 1978, pp. 130.4–1310, it is known that torasemide can occur in two modifications each having a different X-ray crystallography. Both modifications are simultaneously present when a solution of torasemide in petroleum ether/ethanol is slowly evaporated. The crystals, which are characterised not only as prisms with a melting point of 159–161.5° C. but also as leaflets with a melting point of 157.5–160° C., are, however, only described in these literature references with regard to their X-ray crystallographic properties. The modification with the melting point of 159–161.5° C., which is hereinafter referred to as modification I, crystallizes monoclinically in the space group $P2_1/c$ and has a true density of about 1.36, and the modification with the melting point of 157.5–160° C., which is hereinafter referred to as modification II, crystallizes monoclinically in the space group P2/n and has a true density of 1.285.

The modification obtained in the case of the preparation and normal purification by precipitating the torasemide is modification II which usually also results in the case of recrystallisations from other solvents. Since this form, in the case of storage of the pure active material, does not change and, in the case of all purification experiments, forms the predominant form, it was assumed that this modification II was stable.

U.S. Pat. Nos. Reissue 34,672 and 34,580 are based on the discovery that torasemide of modification II, when it is present in very finely divided form in pharmaceutical tablets, rearranges more or less quickly into modification I, whereby the crystal size and speed of dissolving of the active material upon introducing the tablets into water can be significantly changed. Since, as was known, the speed of dissolving represents one of the important characteristics of a pharmaceutical form of administration and thus, in order to be able to dose reproducibly, must not differ from one tablet to another, the problem existed of finding a form of administration of torasemide which does not change its speed of dissolving during storage. Since the uncontrollable change of the speed of dissolving depends upon the rearrangement of modification II into modification I of the torasemide, it was obvious ab initio to use modification I.

From investigations it was found that modification I is stable in tablets and did not rearrange again back into modification II.

SUMMARY OF THE INVENTION

It has now been discovered that a third form of torasemide exists, and we have labeled this third form as modification III. Modification III is stable, and has significantly greater solubility than modification I above pH 3 and especially at a pH of approximately 7.4. This suggests that modification III is especially suitable for use as a diuretic where a rapid onset of diuretic effect is desired, or as a way to avoid intravenous therapy, since oral administration could be used. The present invention is thus directed to torasemide of modification III, a pharmaceutical composition containing pure modification II, the use of torasemide of modification III to cause a diuretic effect, and a process for making torasemide of modification III.

DESCRIPTION OF THE DRAWINGS

The invention will be understood more clearly with reference to the accompanying drawings, wherein.

DETAILED DESCRIPTION OF THE INVENTION

Figure 1:
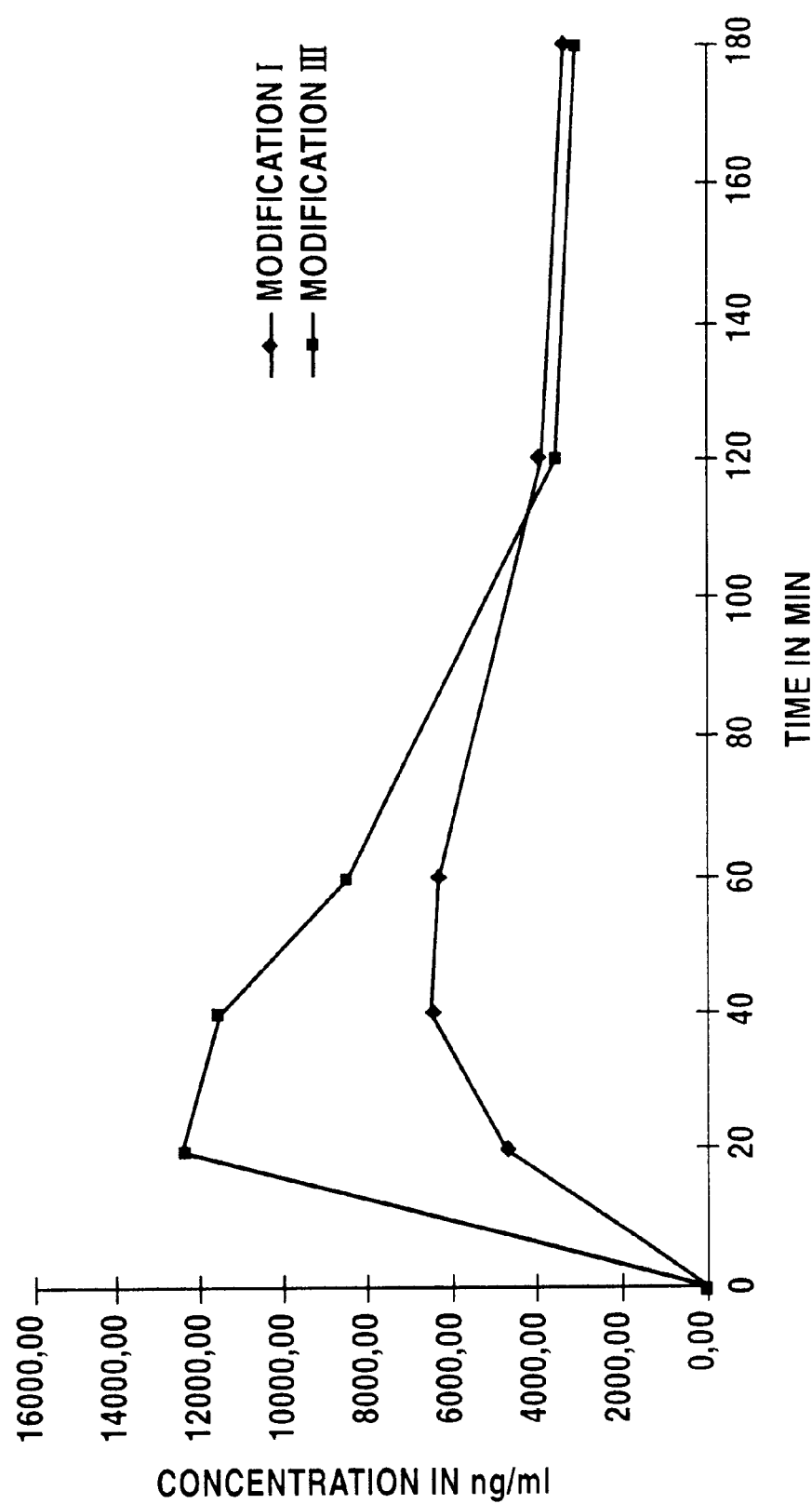
FIG. 1 is a plot of serum concentration levels in male rats of torasemide of modification I and modification III versus time after oral administration.

One aspect of the present invention involves pure torasemide of modification III. It is believed that pure torasemide of modification III was previously unknown to the art. Torasemide of modification III can be characterized by a melting point of 155 to 158° C. (thermomicroscopy) and a true density of $1.302\pm0.009$ g $cm^{-3}$ (versus $1.363\pm0.001$ g $cm^3$ for modification I). In a preferred embodiment, the torasemide of modification III is pure. This term "pure" means that the torasemide contains less than about 1% of modification I and/or II, and less in any event than amounts of modification I which adversely effect the stability of modification III.

The torasemide of modification III is storage stable. By "storage stable" reference is made to the torasemide, when in tablet form and stored under ambient conditions, having less than 5%, preferably less than 2%, of the modification III changing into another crystalline form over a six month period of time.

Another aspect of the present invention is instant release pharmaceutical compositions containing modification III. Oral forms of administration containing torasemide of modification III are produced in the usual way with the use of pharmacologically acceptable adjuvants, for example sugar, starch, starch derivatives, cellulose, cellulose derivatives, mould separation agents and anti-adhesion agents, as well as possibly flow regulation agents. In particular, in the case of the use of torasemide of modification III, aqueous process steps, for example granulation, can be carried out.

It is preferred that the active material torasemide of modification III is used with the following particle size distribution:

at least 90%<96 μm. and, at least 50%<48 μm.

In comparison with pharmaceutical formulations with the active material being torasemide of modification I or II, the formulations according to the present invention have a rapid in vitro rate of dissolving which remains unchanged even after comparatively long storage at temperatures higher than ambient temperature and at a comparatively high atmospheric humidity, and a rapid in vivo appearance, combined with high initial concentrations, of the torasemide in serum, ably then dried to a low moisture content, preferably below about 6%, to produce substantially pure torasemide of modification III.

Relevant data of the two most important crystal forms (modification I and III) of torasemide are summarized in Table 1.

TABLE 1

Characteristic physico-chemical properties of Mod. I and Mod. III of Torasemide

|  | Mod. I | Mod. III |
|---|---|---|
| Habit | prismatic platelets | aggregates |
| Melting point (° C.)  Thermomicroscopy | 158–161 | 155–158 |
| DSC | 161.5[1] | 157.0[1] |
| Heat of fusion (kJ mol$^{-1}$) ± 95% – C.B. | 37.2 ± 1.9[1] | 29.9 ± 0.9[1] |
| Heat of transition (kJ mol$^{-1}$) at about 159° C. ± 95% – C.B. |  | −82 ± 2.1[2] |
| Heat of solution (kJ mol$^{-1}$) in I-butanol at 20° C. | 36.1 | 29.8 |
| First IF-Peak (cm$^{-1}$) | 3353 | 3356 |
| Water content (%) after storing in relative humidity of 92% at 25° C. | 0.2 | 1.2 (depending on particle size |
| Solubility (mmol L$^{-1}$) at 20° C. at pH 4.90 | 0.34 | 0.93 |
| True density (g cm$^{-3}$) ± 95% – c.i. | 1.363 + 0.001 | 1.302 ± 0.009 |

1) heating rate 5K min$^{-1}$
2) the difference of the heats of fusion

The rapid commencing pharmacological action of these compositions is ensured by the rapid rate of dissolving of the active material from the form of administration, such as tablets. As illustrated in FIG. 1, 20 minutes after administration modification III has more than twice the serum concentration as modification I, and after 40 minutes has almost twice the serum concentration as modification I. This rapid appearance of modification III in the serum after oral administration suggests that modification III is particularly suitable for use as a diuretic for the treatment of patients requiring a rapid onset of the diuretic effect.

The torasemide of modification III of the present invention can be prepared from torasemide of modification II and/or modification I. The torasemide of modification II and/or modification I is dissolved in an alkaline aqueous solution to form a solution having a pH of 9—13. The alkaline material in the alkaline aqueous solution is conveniently sodium hydroxide, although potassium hydroxide, and the like alkali metal hydroxides, may be substituted therefor. The resulting alkaline solution is then acidified by the gradual addition of an inorganic acid until a pH of 8.5 or less is reached. The pH upon acidification can be as low as about 4.0 or even less but preferably the acidification is to a pH of about 7.5 to about 8.5. The acid is added to the alkaline solution gradually, conveniently over a period of about 25 minutes, although the time of acid addition can vary from 15 to 60 minutes or more depending on the batch size and the acid/base concentration. It is important to avoid the occurrences of "hot spots" during acidification, and this is readily accomplished by agitation, although other methods of avoiding local high concentrations of acids, which cause such hot spots, are known to the art and can be used. The solution is preferably maintained at a constant temperature between just above the freezing point of the solution and 60° C., and preferably between about 5 to about 40° C., and most preferably at about room temperature. Torasemide of modification III will begin to crystalize from the solution, and the crystallization will be essentially complete after about 10 to about 30 minutes from the initial crystallization. The crystals can be recovered from the aqueous medium by any conventional means, such as filtration, and are prefer- Modification I consists of thin hexa- to octagonal platelets, which start to melt at 158° C. Simultaneously with the end of the melting process at 161° C. the forming of bubbles in the melt can be observed. The remaining crystals in the melt do not grow during cooling. Also, the melt remains amorphous after cooling. On reheating of the glassy melt softening occurs at about 120° C. but no crystallization is observed. During annealing, the melt color turns to brownish.

Modification III consists of aggregates of tiny crystals. The melting process starts at 155° C. and ends at 158° C. The behavior of the melt is analogous to that of modification I.

The torasemide of modification III, like torasemide of modification I or II, is an effective diuretic. Torasemide of modification I has been approved under the brand name Demadex in the U.S. for indications which include essentially hypertension; oedema due to congestive heart failure; and hepatic, pulmonary and renal oedema. Torasemide of modification III is more potent than, and can be used for the same indications as, modification I. For essential hypertension the torasemide will generally be administered orally to adults at a dosage level of from about 2.5 mg to about 5 mg. The initial oral dosage for oedema is generally about five milligrams for an adult, but increasing step wise up to about 20 mg per day if necessary. For intravenous injection, the adult dosage, including that of elderly patients for oedema due to congestive heart failure or of hepatic organ, will normally be about 10 mg per day i.v., and increasing up to about 20 mg daily if required. The maximum recommend dose is 40 mg per day. For oedema of renal organ, the starting dose will normally be about 20 mg of torasemide daily i.v. up to a maximum of 200 mgs of torasemide of modification III daily if required.

While oral administration of torasemide of modification III is preferred, it is also possible to administer the torasemide through intravenous injection, using, for instance, a suitable injectable solution such as that taught by U.S. Pat. No. 4,861,786, the disclosure of which is hereby incorporated by reference for the teachings of such solutions therein. Broadly, the torasemide of modification III will be administered to adult patients at a daily dosage of from about 2 to about 200 mg per day, and preferably 5 to 25 mg per day.

EXAMPLES OF THE INVENTION

The present invention will be understood more readily with reference to the following examples, wherein unless indicated otherwise percentages are percentages by weight.

Example 1

4.0 kg of torasemide of modification II, prepared according to U.S. Pat. No. Reissue 30,633, was dissolved in 12 liters of 1 n aqueous sodium hydroxide. 1 n Aqueous sulfuric acid was gradually added to the solution with stirring until a pH value of 7.5 was reached over a period of about 25 minutes, with the solution being maintained at a temperature of 3° C. The crystallization started, and after about 15 minutes, maintaining the temperature at 3° C., was essentially complete. The crystals were filtered from the aqueous medium and dried to yield 3.85 kg of torasemide of modification III in which no modification I or modification II could be detected.

Example 2

Example 1 was repeated, except the pH value after the sulfuric acid addition was 5.5. The results were similar.

Example 3

Example 1 was repeated, except the pH value after sulfuric acid addition was 6.5. The results were similar.

Example 4

Example 1 was repeated, except the pH value after sulfuric acid addition was 8.5. The results were similar.

Example 5

Example 3 was repeated, except the temperature of the solution before and during crystallization was 25° C. The results were similar.

Example 6

Example 5 was repeated, except the temperature of the solution before and during crystallization was 50° C. The results were similar.

Example 7

Example 1 was repeated, but with 1 n acetic acid being used in place of the sulfuric acid. The solution was acidified to a pH value of 6.5, and the solution temperature was maintained at 25° C. The results were similar.

Example 8

The product of Example 1 was formed into tablets. 10 kg of microfine torasemide of modification III were mixed with 11.6 kg of lactose 90 and 3.5 kg of maize starch. The mixture was granulated by the addition of 24–29 kg of purified water. The moist granules were dried in a fluidized bed dryer, maintaining the product temperature no greater than 50° C., to a water content of 4.5 to 6%. Thereafter a 72 kg of colloidal anhydrous silica and a 48 kg of magnesium stearate were mixed into the mixture and the product was sieved. The resulting product was tableted into Demadex 10 mg tablets having a mass of 160 mg.

ANIMAL TESTS

Figure 2:
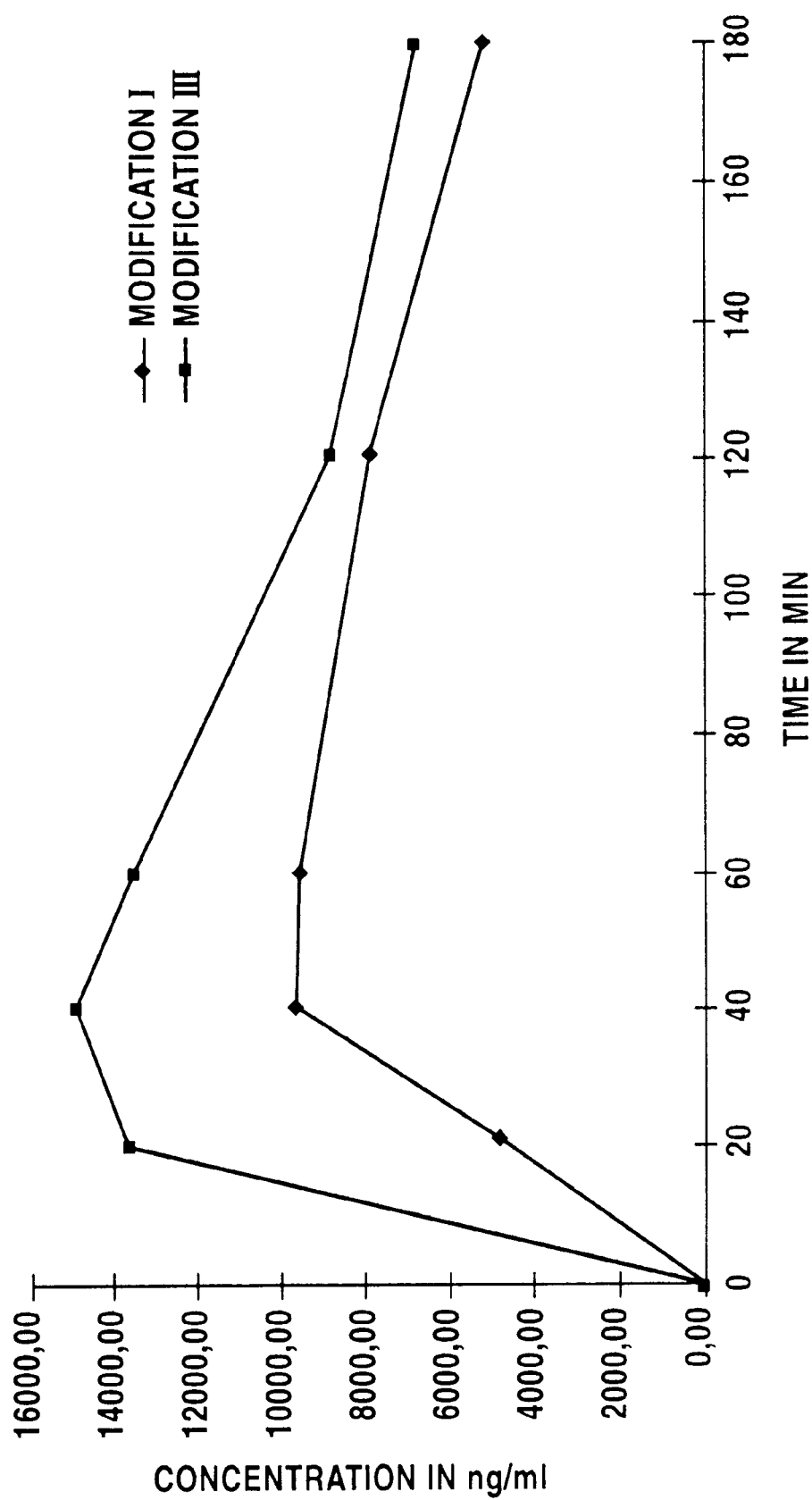
FIG. 2 is similar to FIG. 1, but reflects the serum concentrations in female rats.

Male and female Wistar rates are known to have significant differences in Torasemide drug excretion rate and metabolism of the parent compound (P-450 oxidation products). Therefore, both genders were tested to determine the concentration of torasemide in serum against the time after administration. The dose of torasemide was 3 mg per kilogram, administered orally. FIG. 1 is a graph illustrating the concentration in the serum of male rats of torasemide, as a result of administering modification I and modification III. FIG. 2 is a representation of the concentration of torasemide versus time after administration for the serum of female rats, treated the same as the male rats of FIG. 1.

What is claimed is:

1. Torasemide consisting essentially of modification III.

2. The torasemide of claim 1, wherein the torasemide is substantially free of crystalline torasemide of modifications I and II.

3. A storage-stable, diuretic pharmaceutical composition comprising an effective amount of torasemide consisting essentially of modification III and a pharmacologically acceptable carrier.

4. Composition of claim 3, wherein the composition is in the form of a storage stable tablet.

5. A method of producing a diuretic effect in a patient in need of such effect, said method comprising orally administering to the patient a diuretic-effective amount of torasemide of pure modification III.

6. Method of claim 5, wherein the torasemide is in the form of a storage stable tablet.

7. Method of claim 6, wherein the tablet is substantially free of crystalline torasemide of modification I (monoclinic, space group $P2_1/c$, melting point of about 159° to 161.5° C., in prism form) and modification II (monoclinic, space group $P2/n_1$ melting point of about 157.5° to about 160° C., in leaflet form).

8. A method of making torasemide of modification III comprising dissolving torasemide of modification II and/or modification I in an alkaline aqueous solution to produce a clear solution of torasemide having a pH of about 9 to 13; thereafter acidifying the solution to a pH of 8.5 or less at a temperature of about 3 to 60° C. to crystallize torasemide of modification III from the acidified solution, and recovering pure crystals of torasemide of modification III.

9. Method of claim 8, wherein the solution of torasemide is acidified under conditions of avoidance of hot spots in the solution.

10. Method of claim 9, wherein the hotspots are avoided by agitation of the solution during acidification.

11. Method of claim 9, wherein the solution is acidified by the addition of dilute mineral acid or acetic acid.

12. Method of claim 11, wherein the dilute mineral acid or acetic acid is added over a time of at least 15 minutes.

13. Method of claim 9, wherein the solution is acidified by bubbling carbon dioxide there through.

14. Method of claim 9, wherein the crystallization is conducted at a temperature of about 5 to about 40° C.

15. Method of claim 14, wherein the crystallization is conducted at room temperature.

16. Method of claim 9, wherein the acidification is to a pH of no less than 5.0.

17. Method of claim 16, wherein the solution is acidified to a pH of about 7.5 to about 8.5.

18. The torasemide of claim 1, wherein the torasemide contains less than about 1% of torasemide of Modification I and/or II.

19. The torasemide of claim 1, wherein the torasemide contains less of Modification I which than the amount adversely effects the stability of torasemide of Modification III.

* * * * *